United States Patent [19]

Kallok

[11] Patent Number: 4,479,796

[45] Date of Patent: Oct. 30, 1984

[54] SELF-REGENERATING DRUG ADMINISTRATION DEVICE

[75] Inventor: Michael J. Kallok, New Brighton, Minn.

[73] Assignee: Medtronic, Inc., Minneapolis, Minn.

[21] Appl. No.: 441,888

[22] Filed: Nov. 15, 1982

[51] Int. Cl.³ .............................................. A61M 5/00
[52] U.S. Cl. ........................................ 604/93; 604/8;
604/175; 604/891; 604/84
[58] Field of Search .......... 604/93, 175, 280, 890–892,
604/8–10, 82–85; 3/1, 1 A

[56] References Cited

U.S. PATENT DOCUMENTS

| | | | |
|---|---|---|---|
| 1,654,745 | 1/1928 | Miller | 604/83 |
| 2,811,156 | 10/1957 | Bragg | 604/84 |
| 3,093,831 | 6/1963 | Jordan | 3/1 |
| 3,313,289 | 4/1967 | Kapral | 3/1 X |
| 4,378,016 | 3/1983 | Loeb | 604/891 |
| 4,391,909 | 7/1983 | Lim | 3/1 X |
| 4,424,056 | 1/1984 | Urquhart et al. | 604/85 X |

FOREIGN PATENT DOCUMENTS

WO82/03764 11/1982 World Intel. Prop. Org. ........... 3/1
1479002 7/1977 United Kingdom ...................... 3/1

Primary Examiner—Dalton L. Truluck
Attorney, Agent, or Firm—Reed A. Duthler; Joseph F. Breimayer; John L. Rooney

[57] ABSTRACT

An implantable dispenser for infusing a desired drug into the blood stream. The dispenser is adapted to be spliced into a blood vessel so that blood flows freely through it. Within the dispenser is a replaceable biomass cartridge containing a colony of microorganisms which produce the drug.

10 Claims, 5 Drawing Figures

SELF-REGENERATING DRUG ADMINISTRATION DEVICE

BACKGROUND OF THE INVENTION

1. Field of the Invention

This invention pertains to the field of implantable medical devices, and in particular to implantable drug dispensers.

2. State of the Prior Art

Various types of drug delivery systems are well known in the prior art. The simplest and most common of these systems employs an elevated container attached to a tube which is coupled to a needle inserted into the patient's body. In such a system the rate of flow is controlled by a valve which sets the drip rate of the drug from the container into the tube. This primary disadvantage of this system is the mobility limitation imposed on patients.

Recently, much progress has been made toward the production of completely implantable infusion systems. Most such systems employ a reservoir for containing the drug, a tube leading from the reservoir to a delivery site, and a valve controlling the rate of flow of the drug into the body. Some systems rely on simple diffusion of the drug, however, most systems employ a pumping mechanism to force the drug into the delivery site. Miniaturized roller pumps and pressurized reservoirs are two common approaches to providing such a pumping force.

Common to all of the implantable systems is the need to refill the reservoir at regular intervals. Typically this is accomplished by providing the reservoir with a puncturable septum and mounting the reservoir immediately under the skin so that it may be filled by hypodermic syringe. The necessity to regularly refill the reservoir has an inherent disadvantage in that each time the hypodermic needle pierces the skin and enters the reservoir, it carries with it minute amounts of tissue and debris which contaminate the drug supply and tend to clog the fluid passageways within the dispenser.

In order to contain a sufficient quantity of the drug to provide for release over an extended period of time, the prior art devices are generally filled with a drug in concentrated form. The concentrated form of the drug in some cases leads to crystallization of the drug and blockage of the fluid passageways within the dispenser.

Recently, research has been undertaken which is directed toward the use of body cells cultured outside the body to produce drugs such as insulin. Such research is described in the article "A Hybrid Artificial Pancreas" by Chick, et al., vol. XXI Trans. Amer. Soc. Artif. Int. Organs, 1975. This article discloses that beta cells may be cultured on semipermeable membranes of a type used for artificial kidneys. The particular membrane utilized is fabricated of XM-50 acrylic copolymer with a maximum molecular weight of 50,000 and is manufactured by Amicon Corp. of Lexington, MA. These membranes are permeable to glucose and insulin, as well as to oxygen, carbon-dioxide and water.

SUMMARY OF THE INVENTION

The present invention provides a drug dispenser which is believed to avoid the cited disadvantages of the prior art structures. The present invention describes an implantable drug dispenser which does not require regular refilling because the drug is manufactured within the dispenser. Further, the dispenser is adapted to be spliced in line with a blood vessel, so that blood flows freely through the dispenser at all times, providing for instant dilution of the drug, eliminating clogging problems due to drug crystallization.

The dispenser is designed around a replaceable biomass cartridge. This cartridge contains a colony of microorganisms which produce the desired drug. These microorganisms may be isolated colonies of body cells which produce the desired drug. Alternatively, a colony of a genetically modified bacteria may serve as the source of the desired drug. Recently, the technology of gene splicing has become well known and early successes have been recorded, using modified E. Coli bacteria. For purposes of the present invention, the bacterial colony should be growth-limited to avoid overpopulation of the biomass cartridge.

The desired organisms are contained within a semipermeable membrane capsule. In order to maximize the surface area for delivery of the drug maximizing the diffusion rate of the product into the blood stream it may be desirable to encapsulate colonies of the microorganisms within smaller membrane units within the membrane capsule. These smaller membrane units may take the form of microspheres. The semipermeable membrane capsule surrounds the microspheres and allows for passage of glucose and oxygen carried by the blood stream into the capsule and the passage of bacterial carbon dioxide, water and the drug out of the capsule and into the blood stream. The capsule is mounted within a replaceable biomass cartridge and floats freely therein. The biomass cartridge is, in turn, mounted within a dispenser body adapted for splicing into a blood vessel.

As assembled, the dispenser presents a smooth bore through which blood may flow, bathing the membrane capsule. Dissolved oxygen and glucose flow through the membrane capsule while blood cells and large protein structures such as antibodies flow past the capsule. The central bore of the dispenser is flared at each end to provide a smooth transition from the blood vessel to the dispenser, minimizing clotting and damage to blood cells.

The microorganisms, sustained by glucose and oxygen within the blood, do not require replacement on a regular basis. If replacement of the capsule should become necessary, the dispenser body is constructed so that it may be disassembled and the cartridge containing the membrane capsule removed and replaced with another capsule. A change in the type of drug or in the dosage of the drug may be effected by replacing the cartridge with a second cartridge having organisms adapted to produce a different drug or to produce greater amount of the drug.

Further objects, features and advantages of the invention will become apparent upon a consideration of the following drawings and detailed description.

DETAILED DESCRIPTION OF THE PREFERRED EMBODIMENT

Figure 1:
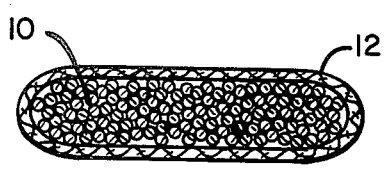
FIG. 1 illustrates a side sectional view of the membrane capsule of the present invention.

FIG. 1 illustrates a side sectional view of the membrane capsule 13 used in the present invention. The membrane capsule consists of membrane 12, formed as an elongated capsule, encloses product producing bacteria or other microorganisms (not illustrated). Membrane 12 may be constructed of materials known to the art, such as the XM-SO acrylic copolymer discussed above. Membranous microspheres 10 float freely within membrane capsule 12, and may be made of the same material. Membrane 12 is of sufficient permeability to allow the passage of water, oxygen and nutrients into the membrane capsule and to allow passage of the product drug and waste products of the microorganisms out of the capsule.

Figure 2:
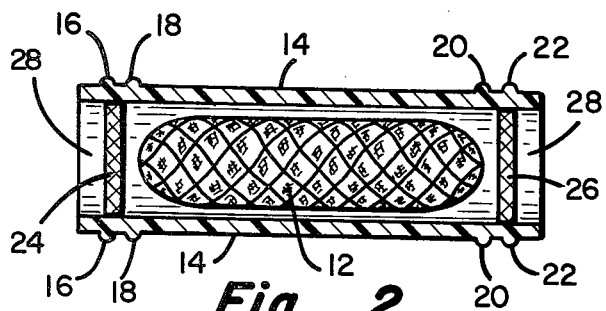
FIG. 2 illustrates a side section view of the cartridge of the present invention.

FIG. 2 illustrates the replaceable biomass cartridge of the present invention. The cartridge consists of a cylindrical cartridge body 14 having a tubular bore 28 running through its length. O-rings 16 and 18 are molded on cartridge body 14 at its proximal end and O-rings 20 and 22 are similarly molded on cartridge body 14 at its distal end. Mounted within bore 28, at each end of cartridge body 14 are retaining screens 24 and 26. Membrane capsule 12 is mounted within cartridge body 14 and is retained therein by screens 24 and 26. Membrane capsule 12 is of smaller diameter than bore 28 so that blood cells and other large structures within the blood incapable of passing through the semipermeable membrane may pass freely through the cartridge body 14. The apertures in screens 24 and 26 are also of sufficient size to permit such passage. In use, membrane capsule 13 floats freely within cartridge body 14. Because the membrane is flexible, but not elastic, membrane capsule 12 is of essentially fixed diameter, preventing blockage of bore 28 by membrane capsule 12.

Cartridge body 14 is preferably a biocompatible, nonthrombogenic plastic such as polyurethane or Teflon ®. Screens 24 and 26 are preferably of similar materials.

The preferred embodiment shows the membrane floating freely within the bore of the cartridge, however, other embodiments wherein the membrane is attached to the cartridge body are believed to be within the scope of the invention.

Figure 3:
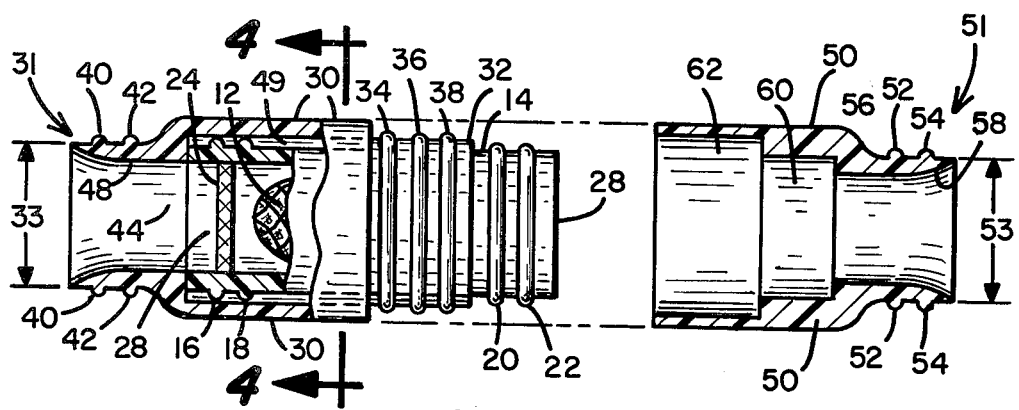
FIG. 3 illustrates a cutaway view of the dispenser and cartridge of the present invention, shown with the dispenser body disassembled.

FIG. 3 illustrates a cut-away view of the present invention. The drawing illustrates the relationship between the cartridge and the dispenser body, and the method of attachment of the dispenser body segments. Cartridge 15 is shown inserted in proximal dispenser body segment 30. Proximal dispenser body segment 30 is provided with a first bore 44 of equal diameter to bore 28 of cartridge body 14. Proximal dispenser body segment 30 is also provided with a second bore 48 which is of equal diameter to O-rings 16 and 18 of cartridge body 14. When inserted, bore 44 aligns with bore 28. The proximal end 31 of proximal dispenser body segment is tapered to an outer diameter 33 of appropriate size for splicing to a blood vessel. By varying diameter 33, the dispenser may be adapted to use in blood vessels of differing sizes. Bore 44 is provided with a smooth flare 46 as illustrated. O-rings 40 and 42 are molded on first dispenser body segment 30 and surround its proximal end 31. At its distal end, proximal dispenser body segment 30 is provided with a reduced diameter segment 32. Distal dispenser body segment 50 is provided with a third bore 56 of equal diameter to bore 28 of cartridge body 14, with a fourth bore 60 which is of equal diameter to O-rings 20 and 22, and with a fifth bore 62 which is of equal diameter to O-rings 34, 36 and 38 of proximal dispenser body segment 30. The distal end 51 of distal dispenser body segment 50 is tapered to an outer diameter 53 of appropriate size for splicing to a blood vessel. Third bore 56 is provided with a smooth flare 58, and distal dispenser body segment 50 is constructed so that the length of fifth bore 62 is equal to the length of reduced diameter segment 32 of proximal dispenser body segment 30 and so that fourth bore 60 is of length equal to the protrusion of cartridge 14 from reduced diameter segment 32. The frictional fit of the O-rings and bores both seals the dispenser and holds it together.

By so constructing the present invention, blood may flow smoothly from the proximal end of proximal dispenser body segment, through cartridge body 14 at the distal end of distal dispenser body segment 50. By providing such a smooth flow path, clotting is minimized and damage to blood cells is reduced. Ramped sections 46 and 54 provide a smooth transition from the blood vessel to the dispenser body. Dispenser body segments 30 and 50 are preferable made of a biocompatible, nonthrombogenic plastic such as polyurethane or Tefon ®.

The preferred embodiment of the dispenser employs O-rings as means for sealing the points of attachment of the dispenser body segments and of the cartridge body and as means for attachment. However, other means of sealing and attachment such as screw threads, are believed to be within the scope of the invention.

Figure 4:
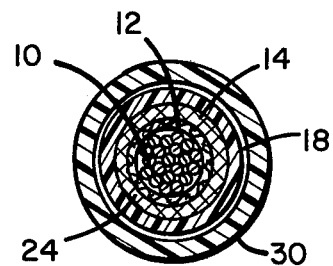
FIG. 4 illustrates a cross-sectional view of the present invention, showing the dispenser body and cartridge body and membrane capsule.

FIG. 4 illustrates a cross-sectional view of the present invention. First dispenser body segment 30, cartridge body 14 and membrane capsule 12 are shown in cross-section. O-ring 18, screen 24, and microsphere 10 are also visible.

Figure 5:
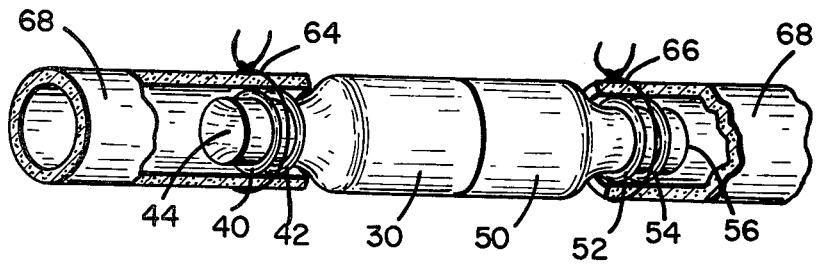
FIG. 5 illustrates the installation of the dispenser in line with a blood vessel.

FIG. 5 shows the present invention as installed in a vein. Vein 64 is severed. One end of vein 64 is pushed over the proximal end 31 of proximal dispenser body segment 30 and the other end of vein 64 is pushed over the distal end 31 of distal dispenser body segment 50. O-rings 40, 42, 52 and 54 provide a fluid seal. Suture 66 is tied around vein 64 between O-rings 40 and 42, stabilizing vein 64 with respect to proximal dispenser body segment 30 and further enhancing the fluid seal. Suture 68 similarly anchors and seals vein 64 to the distal end 31 of distal dispenser body segment 50.

What is claimed is:

1. An implantable drug dispenser comprising:
 a dispenser body having a proximal end and a distal end and a bore running from said proximal to said distal end, said proximal end provided with a first attachment means for attaching said proximal end to a blood vessel, said distal end provided with a second attachment means for attaching said distal end to a blood vessel, said dispenser body further comprised of a cartridge comprising a cartridge body having a proximal end, a distal end, and a central bore connecting said proximal end to said distal end, the bore of said cartridge body in fluid communication with the bore of said dispenser body, wherein said cartridge further comprises retaining means for retaining a colony of drug producing microorganisms within said bore of said dispenser body.

2. An implantable drug dispenser according to claim 1 wherein said retaining means comprises a semipermeable membrane of sufficient permeability to permit passage of nutrients, microorganism waste, and said drug therethrough.

3. An implantable drug dispenser according to claim 2 wherein said semipermeable membrane takes the form of a closed capsule for encapsulating said colony of drug producing microorganisms.

4. An implantable drug dispenser comprising:
a dispenser body having a proximal end and a distal end and a bore running from said proximal to said distal end, said proximal end provided with a first attachment means for attaching said proximal end to a blood vessel, said distal end provided with a second attachment means for attaching said distal end to a blood vessel; and
a retaining means for retaining a colony of drug producing microorganisms within the bore of said dispenser body, comprising a semipermeable membrane of sufficient permeability to permit passage of nutrients, microorganism waste, and said drug therethrough, taking the form of a closed capsule for encapsulating said coloney of drug producing microorganisms, said retaining means further comprising a first screen, spanning the bore of said dispenser body, located proximal to said capsule, said first screen having pores of sufficient size to permit passage of blood cells therethrough and a second screen, spanning the bore of said dispenser body, located distal to said capsule, said second screen having pores of sufficient size to permit passage of blood cells.

5. An implantable drug dispenser according to claim 4 wherein said dispenser body is further comprised of a cartridge comprising a cartridge body having a proximal end, a distal end, and a central bore connecting said proximal end to said distal end, the bore of said cartridge body in fluid communication with the bore of said dispenser body, wherein said cartridge further comprises said retaining means.

6. An implantable drug dispenser according to claim 1 or claim 2 or claim 3 or claim 4 or claim 5 wherein said cartridge is removable from said dispenser body.

7. An implantable drug dispenser according to claim 6 wherein said dispenser body further comprises a proximal dispenser body segment including the proximal end of said dispenser body and a distal dispenser body segment including the distal end of said dispenser body, said proximal dispenser body segment and said distal dispenser body segment enclosing said cartridge.

8. An implantable drug dispenser according to claim 7 wherein said proximal dispenser body segment is removeable from said distal dispenser body segment.

9. An implantable drug dispenser according to claim 8 wherein the bore of said cartridge and the bore of said dispenser body are continuous when said cartridge is installed in said dispenser body.

10. An implantable drug dispenser according to claim 9 wherein the bore of said dispenser body is flared at the proximal end of said dispenser body and flared at the distal end of said dispenser body.

* * * * *